US012672924B2

(12) United States Patent
Axelson et al.

(10) Patent No.: US 12,672,924 B2
(45) Date of Patent: Jul. 7, 2026

(54) METHODS AND SYSTEMS FOR ROBOT-ASSISTED TOTAL KNEE ARTHROPLASTY

(71) Applicant: Encore Medical, LP, Austin, TX (US)

(72) Inventors: Stuart L. Axelson, Succasunna, NJ (US); Alexander Raphe Massa, Basking Ridge, NJ (US); Anthony Joseph La Rosa, Wharton, NJ (US); R. Michael Meneghini, Terre Haute, IN (US); Michael J. Taunton, Rochester, MN (US); Scott M. Sporer, Chicago, IL (US); James A. Browne, Charlottesville, VA (US); Raymond H. Kim, Vail, CO (US)

(73) Assignee: Encore Medical, LP, Austin, TX (US)

( * ) Notice: Subject to any disclaimer, the term of this patent is extended or adjusted under 35 U.S.C. 154(b) by 212 days.

(21) Appl. No.: 18/238,361

(22) Filed: Aug. 25, 2023

(65) Prior Publication Data

US 2024/0065784 A1     Feb. 29, 2024

Related U.S. Application Data

(60) Provisional application No. 63/401,412, filed on Aug. 26, 2022.

(51) Int. Cl.
*A61B 34/30*        (2016.01)
*A61B 17/15*        (2006.01)
(Continued)

(52) U.S. Cl.
CPC ............ *A61B 34/30* (2016.02); *A61B 17/154* (2013.01); *A61B 17/1764* (2013.01); *A61B 34/20* (2016.02); *A61B 2034/2059* (2016.02)

(58) Field of Classification Search
CPC ...................................................... A61B 34/30
See application file for complete search history.

(56) References Cited

U.S. PATENT DOCUMENTS

| | | |
|---|---|---|
| 6,837,892 B2 | 1/2005 | Shoham |
| 6,955,654 B2 | 10/2005 | Gilmour |

(Continued)

FOREIGN PATENT DOCUMENTS

| | | |
|---|---|---|
| AU | 2005216267 B2 | 11/2008 |
| AU | 2004280263 B2 | 11/2010 |

(Continued)

OTHER PUBLICATIONS

Delp, S., et al., "Computer Assisted Knee Replacement." Clinical Orthopaedics and Related Research, Sep. 1, 1998, v. 354, pp. 49-56, https://doi.org/10.1097/00003086-199809000-00007.

(Continued)

*Primary Examiner* — Andrew Yang
(74) *Attorney, Agent, or Firm* — Veros Legal Solutions, LLP

(57) ABSTRACT

Robotic systems for orthopedic surgery are provided. The robotic systems may include at least first and second motors coupled to each other. An output shaft of one of the motors may be connectable to a surgical tool guide. An output shaft of another of the motors may be coupled to a portion of a ball and socket joint. A corresponding portion of the ball and socket joint may be coupled to a bone mount which may be attached to a bone to mount the first and second motors to bone for performing orthopedic surgical procedures.

20 Claims, 10 Drawing Sheets

(51) Int. Cl.
  *A61B 17/17*        (2006.01)
  *A61B 34/20*        (2016.01)

(56)                References Cited

U.S. PATENT DOCUMENTS

| | | | |
|---|---|---|---|
| 7,572,297 | B2 | 8/2009 | Cheal et al. |
| 7,635,369 | B2 | 12/2009 | Cinquin et al. |
| 7,691,108 | B2 | 4/2010 | Lavallee |
| 7,753,960 | B2 | 7/2010 | Cipolletti et al. |
| 7,803,310 | B2 | 9/2010 | Cheal |
| 8,096,997 | B2 | 1/2012 | Plaskos et al. |
| 8,126,533 | B2 | 2/2012 | Lavallee |
| 8,214,016 | B2 | 7/2012 | Lavallee et al. |
| 8,231,631 | B2 | 7/2012 | Lavallee et al. |
| 8,241,293 | B2 | 8/2012 | Stone et al. |
| 8,277,513 | B2 | 10/2012 | Cipolletti et al. |
| 8,337,508 | B2 | 12/2012 | Lavallee et al. |
| 8,532,807 | B2 | 9/2013 | Metzger |
| 8,617,171 | B2 | 12/2013 | Park et al. |
| 8,626,267 | B2 | 1/2014 | Lavallee |
| 8,672,945 | B2 | 3/2014 | Lavallee et al. |
| 8,737,700 | B2 | 5/2014 | Park et al. |
| 8,771,188 | B2 | 7/2014 | Schers et al. |
| 8,801,719 | B2 | 8/2014 | Park et al. |
| 8,808,301 | B1 | 8/2014 | Nofsinger |
| 8,828,087 | B2 | 9/2014 | Stone et al. |
| 8,880,152 | B2 | 11/2014 | Lavallee |
| 8,882,779 | B2 | 11/2014 | Park et al. |
| 8,903,530 | B2 | 12/2014 | Metzger |
| 8,990,052 | B2 | 3/2015 | Lavallee et al. |
| 9,033,958 | B2 | 5/2015 | Mailloux et al. |
| 9,037,295 | B2 | 5/2015 | Hodgson et al. |
| 9,050,132 | B2 | 6/2015 | Lavallee |
| 9,173,665 | B2 | 11/2015 | Couture |
| 9,220,510 | B2 | 12/2015 | Cheal et al. |
| 9,220,571 | B2 | 12/2015 | Lavallee |
| 9,248,001 | B2 | 2/2016 | Colombet et al. |
| 9,351,744 | B2 | 5/2016 | Kunz et al. |
| 9,421,019 | B2 | 8/2016 | Plaskos et al. |
| 9,549,782 | B2 | 1/2017 | Park et al. |
| 9,610,086 | B2 | 4/2017 | Park et al. |
| 9,684,768 | B2 | 6/2017 | Lavallee et al. |
| 9,700,259 | B1 | 7/2017 | Nofsinger |
| 9,730,713 | B2 | 8/2017 | Park et al. |
| 9,737,311 | B2 | 8/2017 | Lavallee et al. |
| 9,757,136 | B2 | 9/2017 | Park et al. |
| 9,757,238 | B2 | 9/2017 | Metzger et al. |
| 9,782,226 | B2 | 10/2017 | Park et al. |
| 9,782,227 | B2 | 10/2017 | Park et al. |
| 9,814,533 | B2 | 11/2017 | Park et al. |
| 9,855,147 | B2 | 1/2018 | Cipolletti et al. |
| 9,861,446 | B2 | 1/2018 | Lang |
| 9,872,733 | B2 | 1/2018 | Shoham et al. |
| 9,883,871 | B2 | 2/2018 | Park et al. |
| 9,889,021 | B2 | 2/2018 | Park et al. |
| 9,980,780 | B2 | 5/2018 | Lang |
| 10,034,678 | B2 | 7/2018 | Park et al. |
| 10,039,558 | B2 | 8/2018 | Park et al. |
| 10,092,361 | B2 | 10/2018 | Ferro et al. |
| 10,159,530 | B2 | 12/2018 | Lang |
| 10,166,002 | B2 | 1/2019 | Schers et al. |
| 10,179,032 | B2 | 1/2019 | Andersson |
| 10,182,870 | B2 | 1/2019 | Park et al. |
| 10,194,990 | B2 | 2/2019 | Amanatullah et al. |
| 10,226,261 | B2 | 3/2019 | Park et al. |
| 10,231,786 | B2 | 3/2019 | Ferro et al. |
| 10,278,777 | B1 | 5/2019 | Lang |
| 10,285,683 | B2 | 5/2019 | Todorov et al. |
| 10,292,768 | B2 | 5/2019 | Lang |
| 10,321,904 | B2 | 6/2019 | Todorov et al. |
| 10,357,315 | B2 | 7/2019 | Otto et al. |
| 10,383,338 | B2 | 8/2019 | Gomelsky et al. |
| 10,383,638 | B2 | 8/2019 | Cheal et al. |
| 10,405,927 | B1 | 9/2019 | Lang |
| 10,441,437 | B2 | 10/2019 | Lavallee et al. |
| 10,449,001 | B2 | 10/2019 | Park et al. |
| 10,449,004 | B2 | 10/2019 | Ferro et al. |
| 10,456,203 | B2 | 10/2019 | Park et al. |
| 10,456,204 | B2 | 10/2019 | Park et al. |
| 10,463,379 | B2 | 11/2019 | Liu et al. |
| 10,470,823 | B2 | 11/2019 | Park et al. |
| 10,499,996 | B2 | 12/2019 | de Almeida Barreto |
| 10,575,875 | B2 | 3/2020 | Pavlovskaia et al. |
| 10,646,285 | B2 | 5/2020 | Siemionow et al. |
| 10,687,856 | B2 | 6/2020 | Pavlovskaia et al. |
| 10,716,643 | B2 | 7/2020 | Justin et al. |
| 10,743,939 | B1 | 8/2020 | Lang |
| 10,806,465 | B2 | 10/2020 | Lavallee et al. |
| 10,849,609 | B2 | 12/2020 | Plaskos et al. |
| 10,849,636 | B2 | 12/2020 | Hafez |
| 10,849,693 | B2 | 12/2020 | Lang |
| 11,266,472 | B2 * | 3/2022 | Pedros ................. A61B 34/30 |
| 2002/0115934 | A1 | 8/2002 | Tuke et al. |
| 2005/0267353 | A1 | 12/2005 | Marquart et al. |
| 2006/0015114 | A1 | 1/2006 | Bernardoni et al. |
| 2006/0122617 | A1 | 6/2006 | Lavallee et al. |
| 2006/0200161 | A1 | 9/2006 | Plaskos et al. |
| 2007/0038223 | A1 | 2/2007 | Marquart et al. |
| 2007/0100346 | A1 | 5/2007 | Wyss et al. |
| 2007/0123896 | A1 | 5/2007 | Wyss et al. |
| 2007/0156157 | A1 | 7/2007 | Nahum et al. |
| 2008/0033571 | A1 | 2/2008 | Tuke |
| 2008/0319448 | A1 | 12/2008 | Lavallee et al. |
| 2009/0043556 | A1 | 2/2009 | Axelson et al. |
| 2010/0130986 | A1 | 5/2010 | Mailloux et al. |
| 2010/0174287 | A1 | 7/2010 | Walker et al. |
| 2010/0217400 | A1 | 8/2010 | Nortman et al. |
| 2011/0130761 | A1 | 6/2011 | Plaskos et al. |
| 2013/0144392 | A1 | 6/2013 | Hughes |
| 2015/0105698 | A1 | 4/2015 | Park |
| 2015/0125060 | A1 | 5/2015 | Park et al. |
| 2015/0148807 | A1 | 5/2015 | Park et al. |
| 2016/0038245 | A1 | 2/2016 | Park et al. |
| 2017/0042557 | A1 | 2/2017 | Plaskos et al. |
| 2017/0056022 | A1 | 3/2017 | Cheal et al. |
| 2017/0312032 | A1 | 11/2017 | Amanatullah et al. |
| 2017/0348008 | A1 | 12/2017 | Lavallee et al. |
| 2018/0296226 | A1 | 10/2018 | Park |
| 2018/0317898 | A1 | 11/2018 | Plaskos et al. |
| 2018/0333207 | A1 | 11/2018 | Moctezuma De la Barrera |
| 2019/0008499 | A1 | 1/2019 | Plaskos et al. |
| 2019/0008500 | A1 | 1/2019 | Plaskos et al. |
| 2019/0008501 | A1 | 1/2019 | Plaskos et al. |
| 2019/0105107 | A1 | 4/2019 | Park et al. |
| 2019/0117239 | A1 | 4/2019 | Verma |
| 2019/0122330 | A1 | 4/2019 | Saget et al. |
| 2019/0142519 | A1 | 5/2019 | Siemionow et al. |
| 2019/0175285 | A1 | 6/2019 | Siemionow et al. |
| 2019/0380792 | A1 | 12/2019 | Poltaretskyi et al. |
| 2020/0000523 | A1 | 1/2020 | Ferro et al. |
| 2020/0038112 | A1 | 2/2020 | Amanatullah et al. |
| 2020/0069376 | A1 | 3/2020 | Garcia et al. |
| 2020/0229877 | A1 | 7/2020 | Siemionow et al. |
| 2020/0261119 | A1 | 8/2020 | Pavlovskaia et al. |
| 2020/0323561 | A1 | 10/2020 | Park et al. |
| 2020/0337734 | A1 | 10/2020 | Park et al. |
| 2020/0375666 | A1 | 12/2020 | Murphy et al. |
| 2021/0315590 | A1 | 10/2021 | Chappuis et al. |

FOREIGN PATENT DOCUMENTS

| | | |
|---|---|---|
| AU | 2006259555 B2 | 3/2011 |
| AU | 2012217694 B2 | 1/2016 |
| AU | 2016235175 B2 | 9/2020 |
| CA | 2954125 C | 9/2018 |
| DE | 10003533 A1 | 8/2001 |
| DE | 112004001893 B4 | 9/2006 |
| EP | 1861051 B1 | 3/2010 |
| EP | 2558010 A1 | 2/2013 |
| EP | 2845547 B1 | 3/2015 |
| EP | 2882368 A1 | 6/2015 |
| EP | 1890864 B1 | 12/2015 |
| EP | 3273854 A1 | 1/2018 |
| EP | 3426179 A1 | 1/2019 |

(56)     References Cited

FOREIGN PATENT DOCUMENTS

| | | | |
|---|---|---|---|
| EP | 3443888 | A1 | 2/2019 |
| EP | 3443924 | A1 | 2/2019 |
| EP | 3445048 | A1 | 2/2019 |
| EP | 3609424 | A1 | 2/2020 |
| EP | 2863820 | B1 | 10/2020 |
| EP | 3273868 | B1 | 11/2020 |
| JP | 4608497 | | 1/2011 |
| WO | 2012024323 | A2 | 2/2012 |
| WO | 2018189725 | A1 | 10/2018 |
| WO | 2018200767 | A1 | 11/2018 |
| WO | 2019052622 | A1 | 3/2019 |
| WO | 2019084331 | A1 | 5/2019 |
| WO | 2019141704 | A1 | 7/2019 |
| WO | 2019245849 | A1 | 12/2019 |
| WO | 2019245851 | A1 | 12/2019 |
| WO | 2019245865 | A1 | 12/2019 |
| WO | 2019245867 | A1 | 12/2019 |
| WO | 2020037308 | A1 | 2/2020 |
| WO | 2020102665 | A1 | 5/2020 |
| WO | 2024044384 | A1 | 2/2024 |

OTHER PUBLICATIONS

D'souza, M. et al., "Robotic-Assisted Spine Surgery: History, Efficacy, Cost, and Future Trends." Robotic Surgery: Research and Reviews, 2019, pp. 9-23, v. 6, http://doi.org/10.2147/RSRR. S190720.

International Preliminary Report mailed on Patentability on Mar. 13, 2025 in PCT/US23/31190.

International Search Report and Written Opinion mailed Jan. 29, 2024 in PCT/US2023/031190.

Shalhoub, S. et al., "Development of an Active Soft-Tissue Balancing System for Robotic-Assisted Total Knee Arthroplasty." Handbook of Robotic and Image-Guided Surgery. 2020, pp. 459-473, Elsevier Inc., https://doi.org/10.1016/B978-0-12-814245-5.00027-X.

Shoham, M. et al., "Bone-Mounted Miniature Robot for SurgicalProcedures: Concept and Clinical Applications." IEEE Transactions on Robotics and Automation, Oct. 2023, pp. 893-901, v. 19, n. 5, https://www.researchgate.net/publication/3299389. Abstract Only.

Sugano, N. "Computer-assisted Orthopedic Surgery." Journal of Orthopaedic Science, May 1, 2003, v. 8(3), pp. 442-448, https://doi.org/10.1007/s10776-002-0623-6.

* cited by examiner

METHODS AND SYSTEMS FOR ROBOT-ASSISTED TOTAL KNEE ARTHROPLASTY

BACKGROUND

Robotics are increasingly being used in surgical procedures, with orthopedic surgeries being one significant application. For example, in a total knee arthroplasty (TKA) procedure, several cuts are performed to configure the end of the femur for attachment of an implant. There are several commercially available robotic platforms in use today, all with the common goal of providing more accurate implant placement and bone preparation in an effort to improve clinical outcomes such as implant longevity. However, these floor-mounted and bone-mounted systems have several drawbacks. Improvements to such systems in terms of size, weight, and ease of use are desired.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

In some embodiments, a robotic system for orthopedic surgery comprises a first motor comprising a first motor shaft defining a first rotation axis, a first output drive shaft coupled to the first motor shaft, a second motor coupled to the first motor and comprising a second motor shaft defining a second rotation axis parallel to the first rotation axis, a second output drive shaft coupled to the second motor shaft, a surgical tool or surgical tool guide integral with, coupled to, and/or configured to be coupled to an end of the first output drive shaft, and a first portion of a ball and socket joint integral with, coupled to, and/or configured to be coupled to an end of the second output drive shaft.

In another embodiment, a robotic system for orthopedic surgery comprises one or more non-sterile motors, one or more non-sterile output shafts driven by the one or more motors, a housing with a sterilized outer surface surrounding the one or more motors and the one or more output shafts, one or more surgical tool or surgical tool guide entry ports in the housing positioned adjacent to ends of the one or more non-sterile output shafts.

In another embodiment, a robotic system for orthopedic surgery comprises at least one motor, at least one motor output shaft coupled to the at least one motor, wherein the at least one motor output shaft comprises a non-circular strain wave generator, a stationary circular ring gear around the at least one motor output shaft, a deformable gear positioned between the stationary circular ring gear and the non-circular strain wave generator, an output shaft integral with, coupled to, and/or configured to be coupled to the deformable gear, and a surgical tool or surgical tool guide integral with, coupled to, and/or configured to be coupled to the deformable gear.

Embodiments further include a surgical tool guide configured for coupling to a motor shaft for robotic surgery, wherein the surgical tool guide comprises a saw guide and a drill guide integral with, fixedly attached, or removably attached to the saw guide.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention. Implementations of the technology described herein are directed generally to robotic systems for performing orthopedic surgery.

Figure 1:
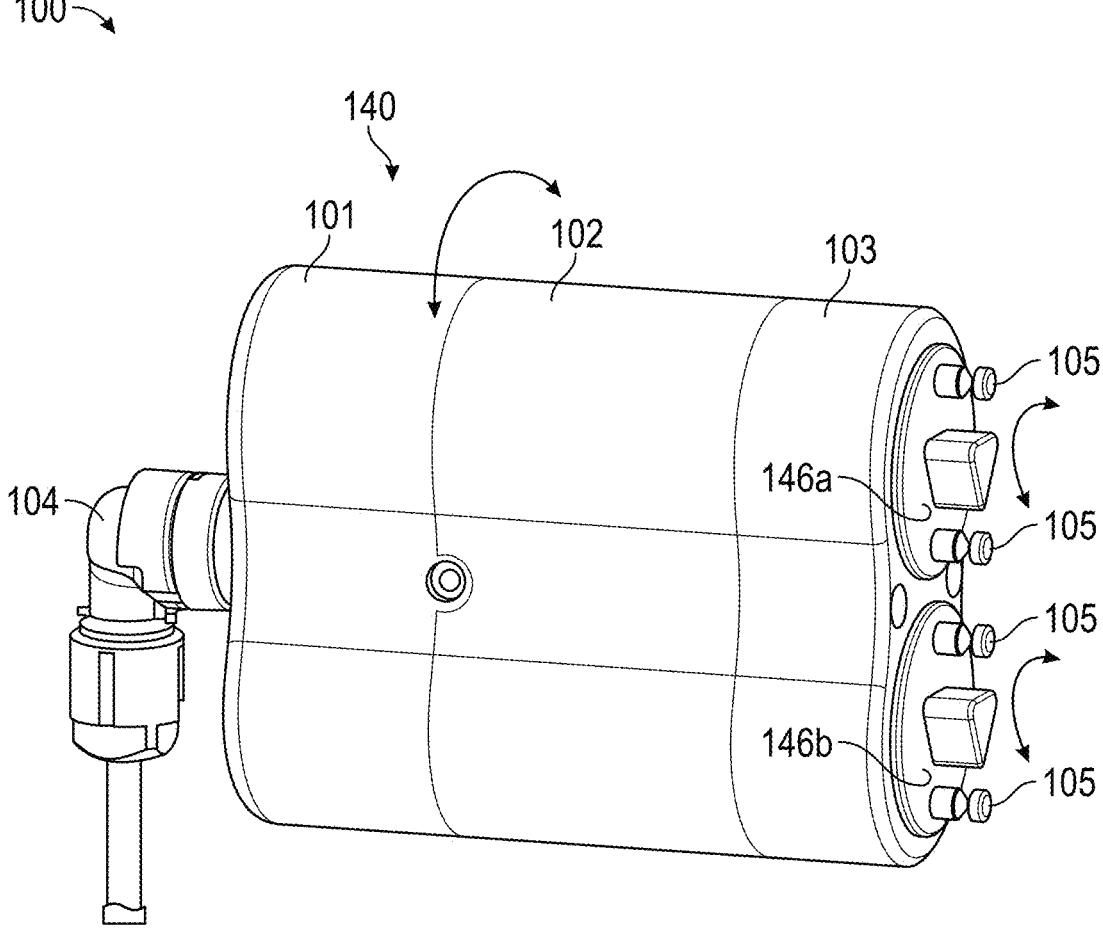
FIG. 1 illustrates a motor pack of a robotic system for orthopedic surgery, in accordance with some example embodiments.

FIG. 1 illustrates a robotic system for orthopedic surgery 100, which may comprise one or more motors. The robotic system may comprise a plurality of motors coupled to one another in a variety of ways. In these embodiments, the motors may be referred to collectively herein as a motor pack 140. In the embodiment of FIG. 1, motor pack 140 comprises a housing configured to encase components of motor pack 140. In some embodiments, the housing comprises a position encoder housing portion 101, a motor housing portion 102, and a gearbox housing portion 103. Portions 101, 102, 103 may be configured to be removably or permanently coupled together to form the motor pack housing. In some embodiments, two or more of housing portions 101, 102, 103 may be integrally formed as a single piece and configured to couple with the remaining portion (if any) to form the motor pack housing shown in FIG. 1.

Motor pack 140 is electrically coupled to power and/or control cables 104 configured to provide electrical power and control signals to motor pack 140 and/or to one or more components thereof. In some embodiments, such electrical power and control signals may be supplied by a control terminal (not shown), which may be configured to receive input and/or other interaction from a surgeon or other user via one or more input devices (e.g., keyboards, joysticks, touchscreens, etc.), to utilize such input to prepare for and/or perform a surgical procedure, and/or to provide visual, auditory, haptic and/or any other type of feedback and/or output via one or more output devices (e.g., screens, speaker, audible tone generators, vibrating modules, etc.).

Motor pack 140 comprises a first output drive shaft 146a configured to rotate with respect to motor pack 140 and a second output drive shaft 146b configured to rotate with respect to motor pack 140, independent of rotation of first output drive shaft 146a. Such rotation is illustrated by the respective double headed arrows about drive shafts 146a, 146b. In the embodiments of FIGS. 1-4, each of first and second output drive shafts 146a, 146b comprise at least one lug 105. Each lug 105 has a first end disposed in a respective aperture of the respective output drive shaft 146a, 146b and a second end configured to engage with one of a surgical tool or surgical tool guide 190 (see, e.g., FIG. 2) or a portion of a ball and socket joint adjustment and locking mechanism 170 (see, e.g., FIG. 2).

As will be described in more detail in connection with one or more figures, one application of the robotic system for orthopedic surgery 100 is in total knee arthroplasty. In this application, rotation of first output drive shaft 146a (via rotation of a motor shaft of a cut guide orientation motor 120 driving it) may cause adjustment of an angular orientation of surgical tool guide 190 with respect to motor pack 140, while rotation of second output drive shaft 146b (via rotation of a motor shaft of a cut guide position motor 125 driving it) may cause adjustment of an angular orientation of motor pack 140, itself, with respect to a bone 200 of the patient to which second output drive shaft 146b is fixed, through ball joint adjustment and locking mechanism 170 and a bone mount 180 (see, e.g., FIG. 2). Such rotation of motor pack 140 with respect to bone 200 is illustrated by the double headed arrow about motor pack 140.

Figure 2:
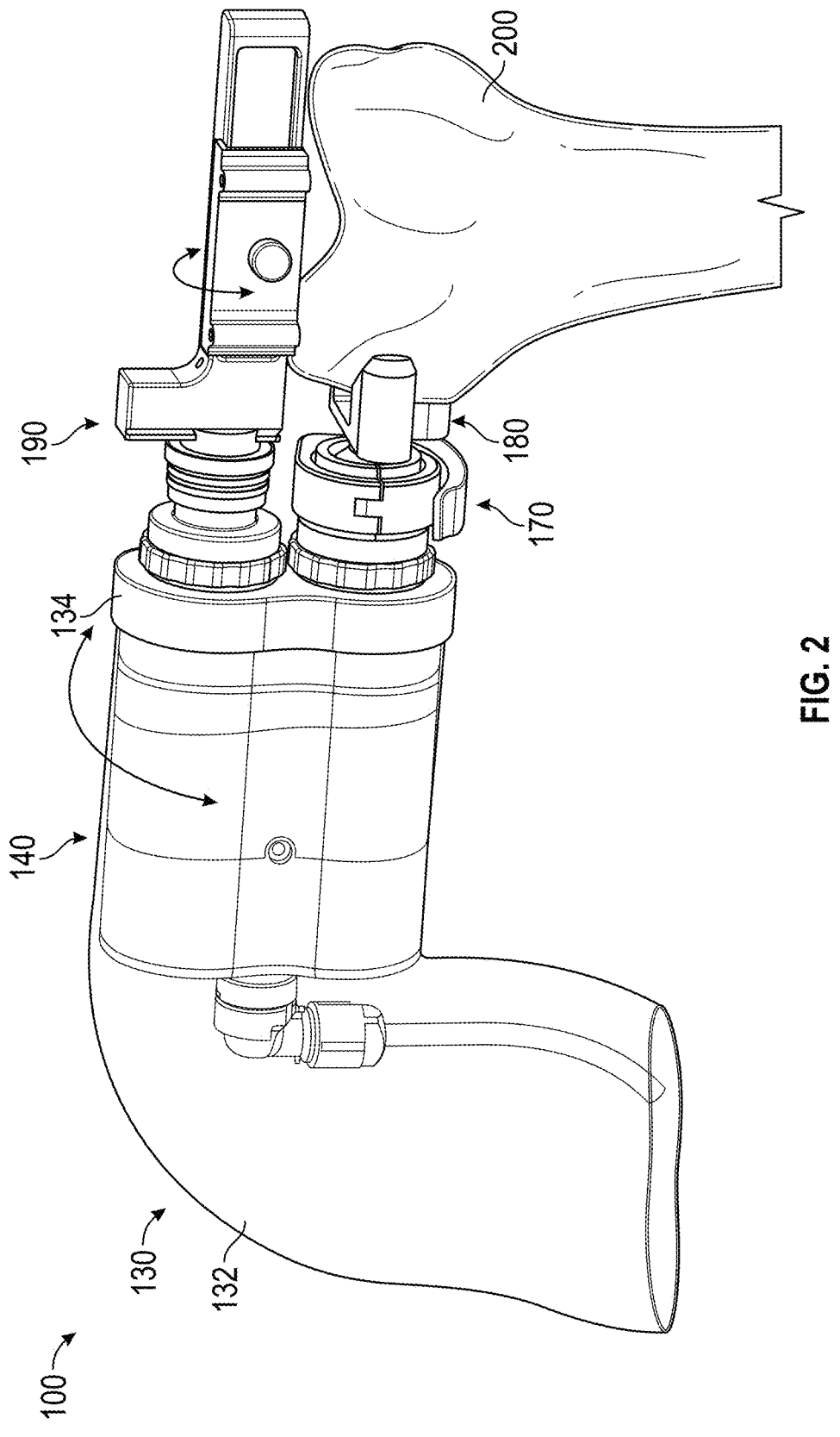
FIG. 2 illustrates the robotic system of FIG. 1 including a sterile barrier, surgical cut guide, ball joint adjustment and locking mechanism, and a bone mount, in accordance with some example embodiments.

FIG. 2 illustrates robotic system 100 of FIG. 1 in a knee arthroplasty application illustrating a surgical tool guide 190, ball joint adjustment and locking mechanism 170, and bone mount 180, in accordance with some example embodiments. In the embodiment of FIG. 2, the motor pack 140 is covered with a sterile shroud 130. Sterile shroud 130 may comprise a flexible shroud 132 coupled to a collar 134. In some embodiments, collar 134 may be rigid and configured to be coupled to, or against, a distal end of motor pack 140, while shroud 134 is configured to extend proximally from collar 134, covering motor pack 140 and at least a portion of power and control cables 104. As shown in FIG. 2 but illustrated in greater detail in at least FIG. 4, first and second output drive shafts 146a, 146b are configured to respectively couple to surgical tool guide 190 and ball joint adjustment and locking mechanism 170, through respective first and second apertures 136, 138 of collar 134.

Figure 3:
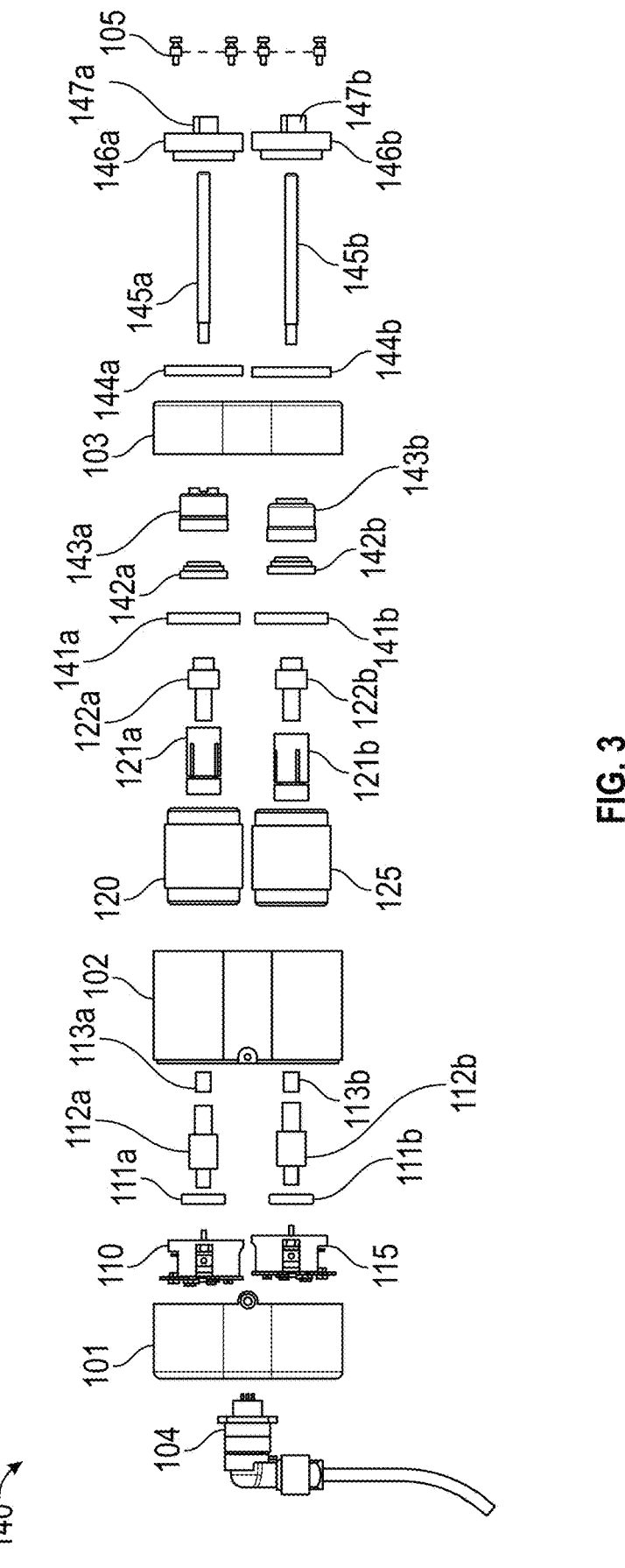
FIG. 3 illustrates an exploded side view of the motor pack of FIG. 1, in accordance with some example embodiments.

FIG. 3 illustrates an exploded side view of motor pack 140 of FIG. 1, in accordance with some example embodiments. Position encoder housing portion 101 comprises a first position encoder 110 and a second position encoder 115. In some embodiments, first position encoder 110 is coupled to a cut guide orientation motor 120 by a first shaft 112a. In some embodiments, first shaft 112a couples to first position encoder 110 through a first bearing 111a and to cut guide orientation motor 120 utilizing a first bushing 113a. First position encoder 110 is configured to measure and/or determine a relative angular orientation of surgical cut guide assembly 190 with respect to motor pack 140. Similarly, in some embodiments, second position encoder 115 is coupled to a cut guide position motor 125 by a second shaft 112b. In some embodiments, second shaft 112b couples to second position encoder 115 through a second bearing 111b and to cut guide position motor 125 utilizing a second bushing 113b. Second position encoder 115 is configured to measure and/or determine a relative angular orientation of motor pack 140, itself, with respect to a bone 200 of the patient, to which second output shaft coupler 146b is ultimately fixed.

Cut guide orientation motor 120 is coupled to a first input shaft 122a for a harmonic gear reduction drive disposed within harmonic gear reduction housing portion 103. In some embodiments, first input shaft 122a is coupled to cut guide orientation motor 120 through a first bushing 121a. Similarly, cut guide position motor 125 is coupled to a second input shaft 122b for the harmonic gear reduction drive disposed within harmonic gear reduction housing portion 103. In some embodiments, second input shaft 122b is coupled to cut guide position motor 125 through a second bushing 121b.

The harmonic gear reduction drive comprises a first assembly for cut guide orientation motor 120 and a second assembly for cut guide position motor 125. Each harmonic gear reduction assembly is configured to provide a high-ratio reduction in rotation speed from its respective motor input to its output.

The first assembly comprises a wave generator 142a within flex spline 143a. This subassembly is coupled to circular spline 141a which is mounted to housing 103. Output shaft 145a then couples the aforementioned subassembly with output shaft coupler 146a via post 147a all within bearing 144a which is mounted to housing 103.

The second assembly comprises a wave generator 142b within flex spline 143b. This subassembly is coupled to circular spline 141b which is mounted to housing 103. Output shaft 145b then couples the aforementioned subassembly with output shaft coupler 146b via post 147b all within bearing 144b which is mounted to housing 103.

Moreover, as illustrated in at least FIG. 3, in some embodiments, first and second output shaft couplers 146a, 146b comprise respective first and second posts 147a, 147b extending distally therefrom. In some such embodiments, first and seconds posts 147a, 147b are configured to be releasably coupled within mating apertures in surgical cut guide assembly 190 and ball joint adjustment and locking mechanism 170, respectively. In some embodiments, first and second posts 147a, 147b have substantially triangular cross-sections. However, the present disclosure is not so limited and first and second posts 147a, 147b may have any suitable cross section(s).

Figure 4:
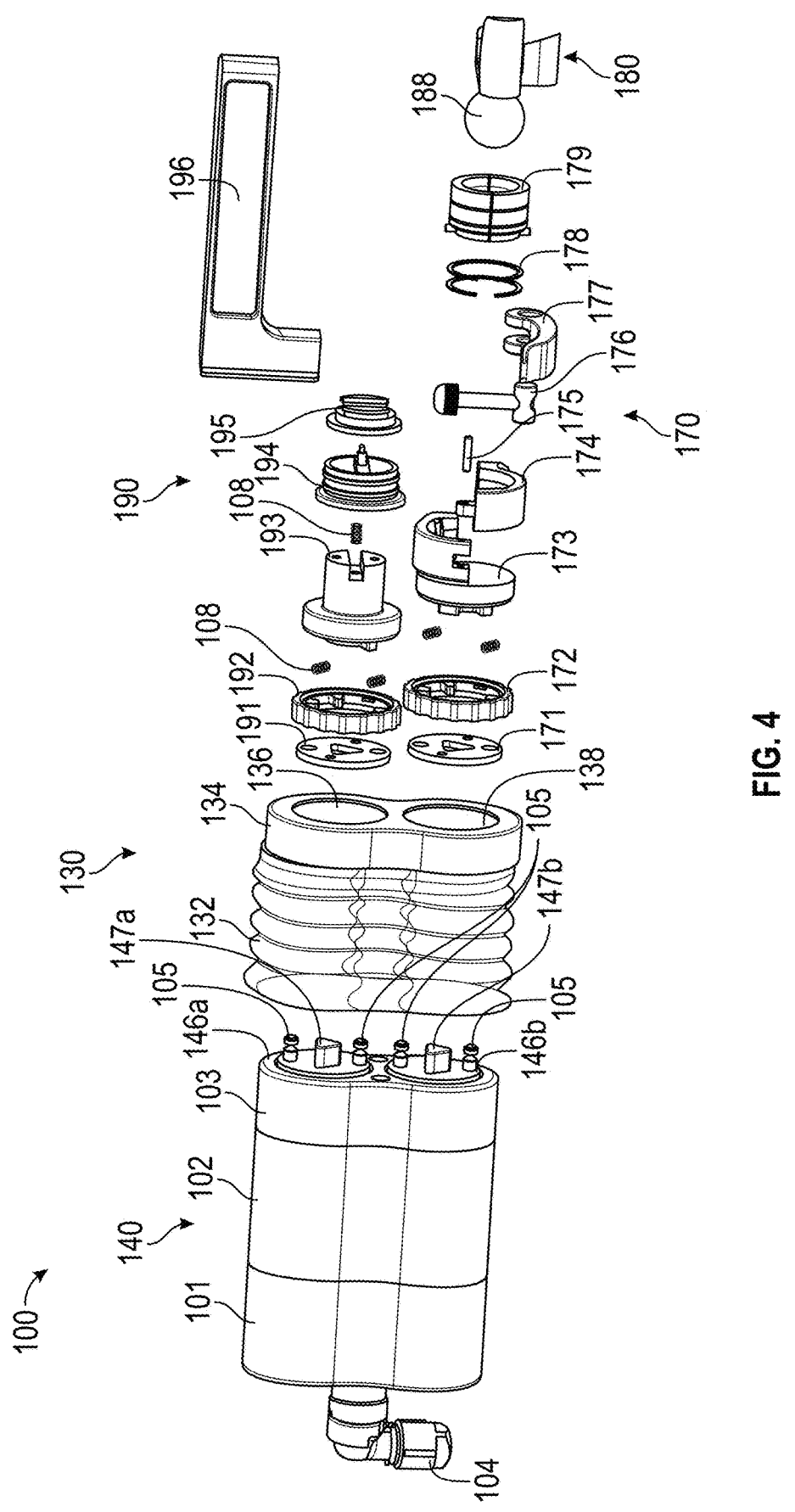
FIG. 4 illustrates an exploded perspective view of the sterile barrier, surgical cut guide, ball joint adjustment and locking mechanism, and bone mount of FIG. 2, in accordance with some example embodiments.

FIG. 4 illustrates an exploded perspective view of sterile barrier 130, surgical cut guide assembly 190, ball joint adjustment and locking mechanism 170, and bone mount 180 of FIG. 2, in accordance with some example embodiments. Motor pack 140 is assembled in FIG. 4. Flexible sterile shroud 132 is disposed over motor pack 140 and collar 134 is disposed against a distal end of motor pack 134 such that first and second output shaft couplers 146a, 146b are disposed at least partially within first and second apertures 136, 138 of collar 134. In some embodiments, such nesting also provides the function of properly aligning motor pack 140 and collar 134 of sterile barrier 130.

Surgical cut guide assembly 190 comprises a docking plate 191. Docking plate 191 comprises a complementary-shaped central aperture, configured to accept first post 147a of first output shaft coupler 146a, and a plurality of peripheral apertures, each configured to receive one of lugs 105 of first output shaft coupler 146a. Surgical cut guide assembly 190 further comprises a locking ring 192 configured to rotate and, thereby, lock assembly 190 into an engaged position on first output shaft coupler 146a.

Surgical cut guide assembly 190 comprises a cutting guide 196 having a slot that allows a cutting blade (not shown) to be disposed therein and guided within narrow tolerances while cutting a portion of a bone 200 of a patient (see FIG. 2). Cutting guide 196 is coupled to a cutting guide holder 195, which comprises a slot configured to secure cutting guide 196 therein. Cutting guide holder 195 is coupled to an intermediate coupler 194, which is coupled to a cutting guide body 193. Various springs 108 may also be utilized within assembly 190. At least a proximal end of cutting guide body 193 is configured to receive distal ends of lugs 105 (and in some embodiments also post 147a) of first output shaft coupler 146a. When these distal ends of lugs 105 are disposed within the proximal end of cutting guide body 193 and locking ring 192 is rotated to a locked position, locking ring 192 and cutting guide body 193 cooperate to retain these distal ends of lugs 105 and, thereby, releasably couple assembly 190 to first output shaft coupler 146a. While not shown, assembly 190 may further comprise a drill guide (not shown) integral with, fixedly attached, or removably attached to cutting guide 196.

Ball joint adjustment and locking mechanism 170 comprises a docking plate 171. Docking plate 171 comprises a complementary-shaped central aperture configured to accept second post 147b of second output shaft coupler 146b and a plurality of peripheral apertures, each configured to receive one of lugs 105 of second output shaft coupler 146b. Ball point adjustment and locking mechanism 170 further comprises a locking ring 172 configured to rotate and, thereby, lock mechanism 170 into an engaged position on second output shaft coupler 146b.

Figure 5:
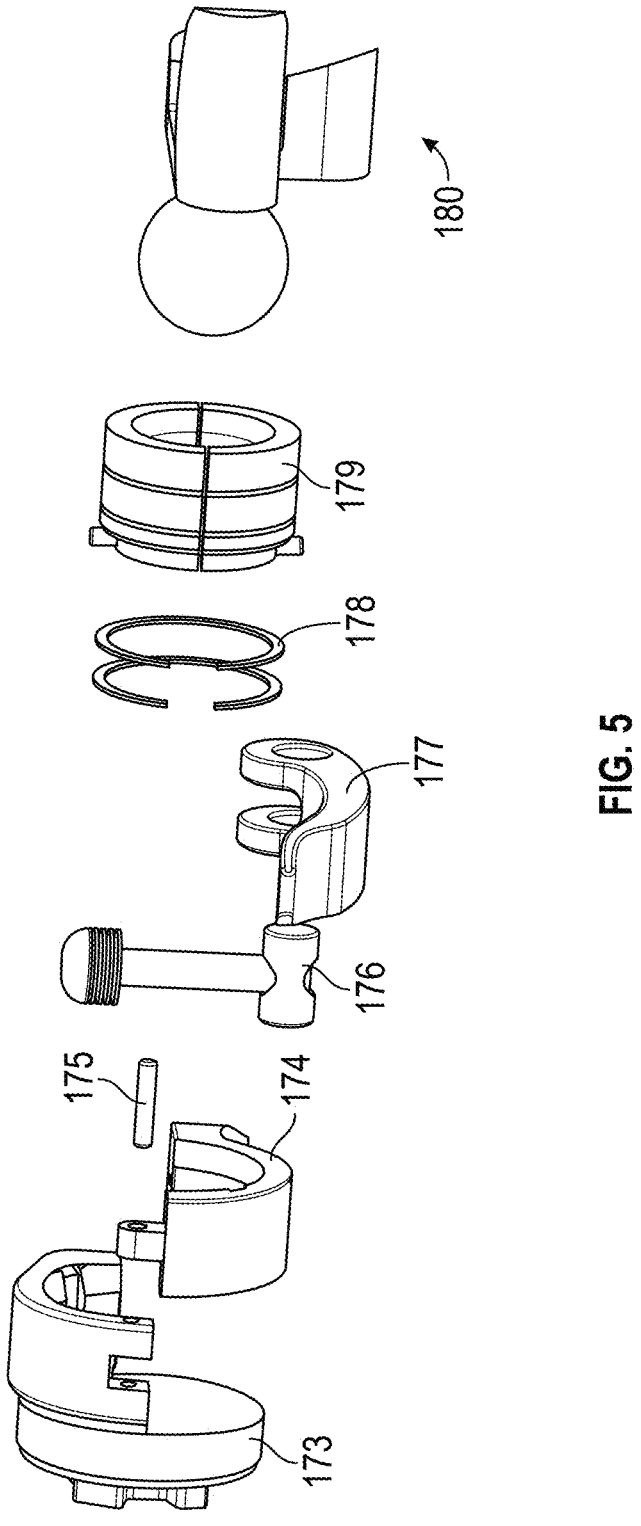
FIG. 5 illustrates an exploded perspective view of the ball joint adjustment and locking mechanism, and bone mount as shown in FIG. 4.

Turning to FIG. 5, which shows a portion of FIG. 4 in greater detail, ball joint adjustment and locking mechanism 170 comprises a socket portion 179 configured to receive a ball portion 188 of bone mount 180 therein. In some embodiments, socket portion 179 comprises a plurality of circumferential grooves configured to receive C-shaped spring clips 178. C-shaped spring clips 178 are configured to provide a clamping force to socket portion 179 as described further below.

Ball joint adjustment and locking mechanism 170 comprises a first locking portion 173 pivotally coupled to a second locking portion 174 by a hinge pin 175. Ball joint adjustment and locking mechanism 170 further comprises a locking lever 177. In some embodiments, locking lever 177 comprises a lobed or cammed surface to provide a locked position and an unlocked position of locking lever 177. When locking lever 177 is disposed in the locked position, first and second locking portions 173, 174 are clamped down on socket portion 179 by lock pin 176 with sufficient force to solidly clamp socket portion 179 around ball portion 188 of bone mount 180 in a desired orientation. In some embodiments, ball portion 188, the inner dimensions of socket portion 179, and spring clips 178 are configured such that ball portion 188 and socket portion 179 are friction-fit stabilized prior to placing locking lever 177 in the locked position. The friction fit stabilization may allow a surgeon to adjust the relative orientations of the motor pack 140 and bone 200 by hand with the ball and socket joint engaged but not locked but wherein the surgeon can let go of the motor pack without disturbing the orientation due to the friction between the ball portion 188 and socket portion 179 generated by the spring clips 178.

At least a proximal end of first locking portion 173 is configured to receive distal ends of lugs 105 (and in some embodiments also post 147b) of second output drive shaft 146b. When these distal ends of lugs 105 are disposed within the proximal end of first locking portion 173 and locking ring 172 is rotated to the locked position, locking ring 172 and first locking portion 173 cooperate to retain these distal ends of lugs 105 and, thereby, releasably couple mechanism 170 to second output drive shaft 146b.

Figure 6:
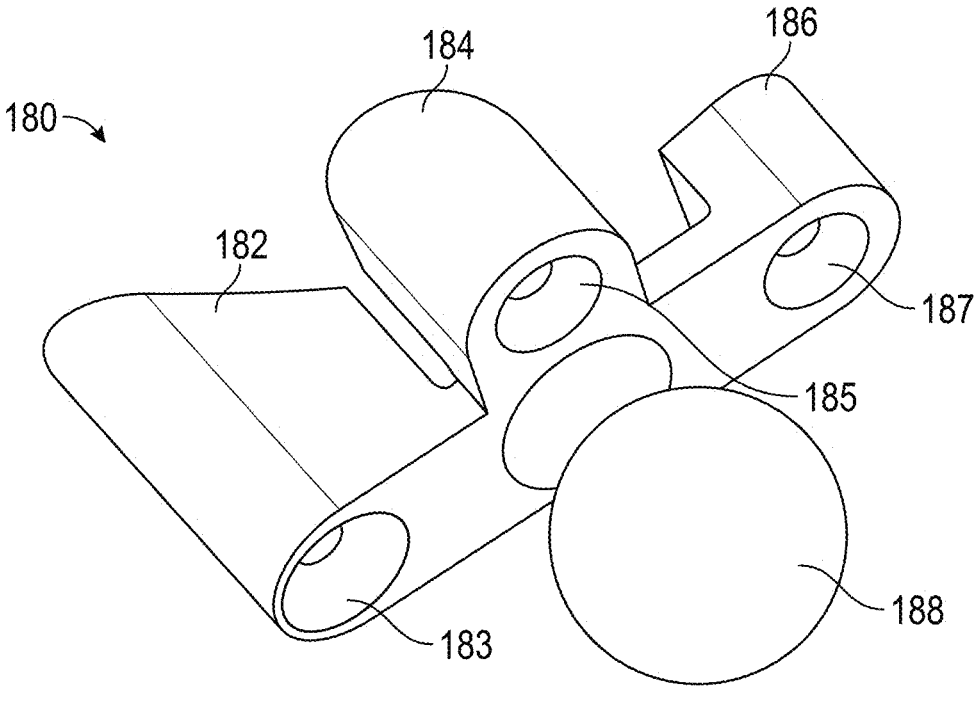
FIG. 6 illustrates the bone mount of FIGS. 2, 4 and 5.

FIG. 6 illustrates bone mount 180 configured to interact with ball joint adjustment and locking mechanism 170, in accordance with some example embodiments. Bone mount 180 comprises a plurality of wings 182, 184, 186, each comprising an aperture 183, 185, 187 configured to receive a bone screw (e.g., an osteocentric 5.2 mm×65 mm cancellous bone screw) therethrough for fixing bone mount 180 against bone 200 of the patient (see, e.g., FIG. 2). In some embodiments, bone mount 180 is formed as a monolithic, single integral piece. In some embodiments, a bone-facing surface of bone mount 180, e.g., a bone-facing surface of one or more of wings 182, 184, 186, may have a shape that is substantially complementary to a portion of bone 200 against which bone mount 180 is configured to be fixed, e.g., having an arcuate bone-facing surface and/or shape. In this way greater mutual contact surfaces of bone 200 bone-facing surface of bone mount 180 may be achieved when bone mount 180 is properly fixed against bone 200. In some embodiments, a surface opposite the bone-facing surface of wings 182, 184, 186 may be substantially flat, i.e., planar. In some embodiments, ball portion 188 is formed to extend away from the surface opposite the bone-facing surface of bone mount 180.

Figure 7:
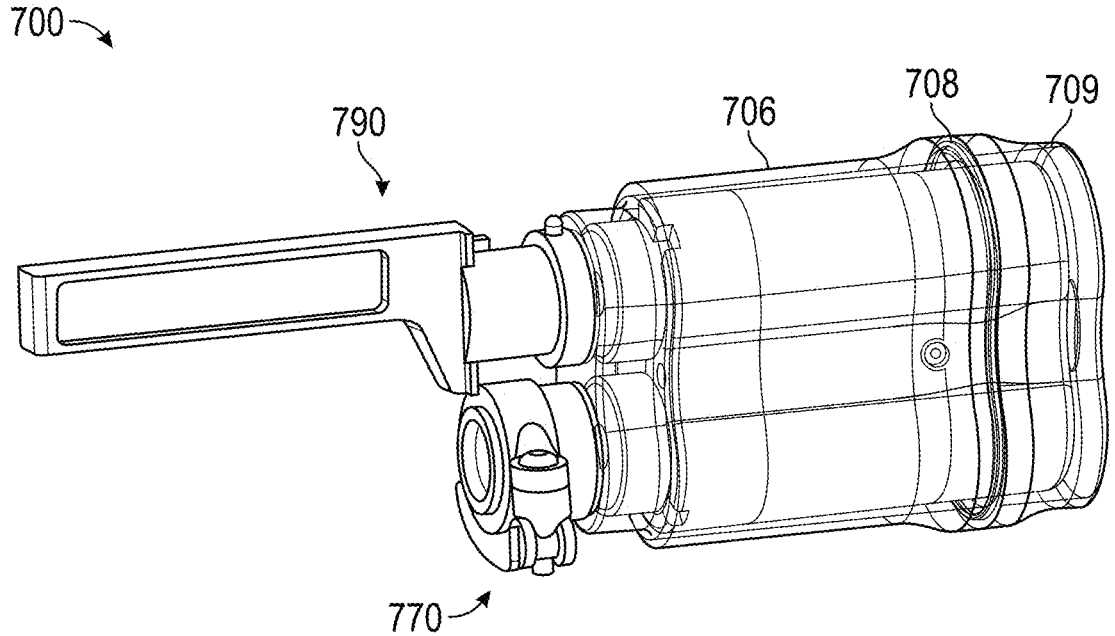
FIG. 7 illustrates a perspective view of a robotic system for orthopedic surgery, in accordance with some example embodiments.
Figure 8:
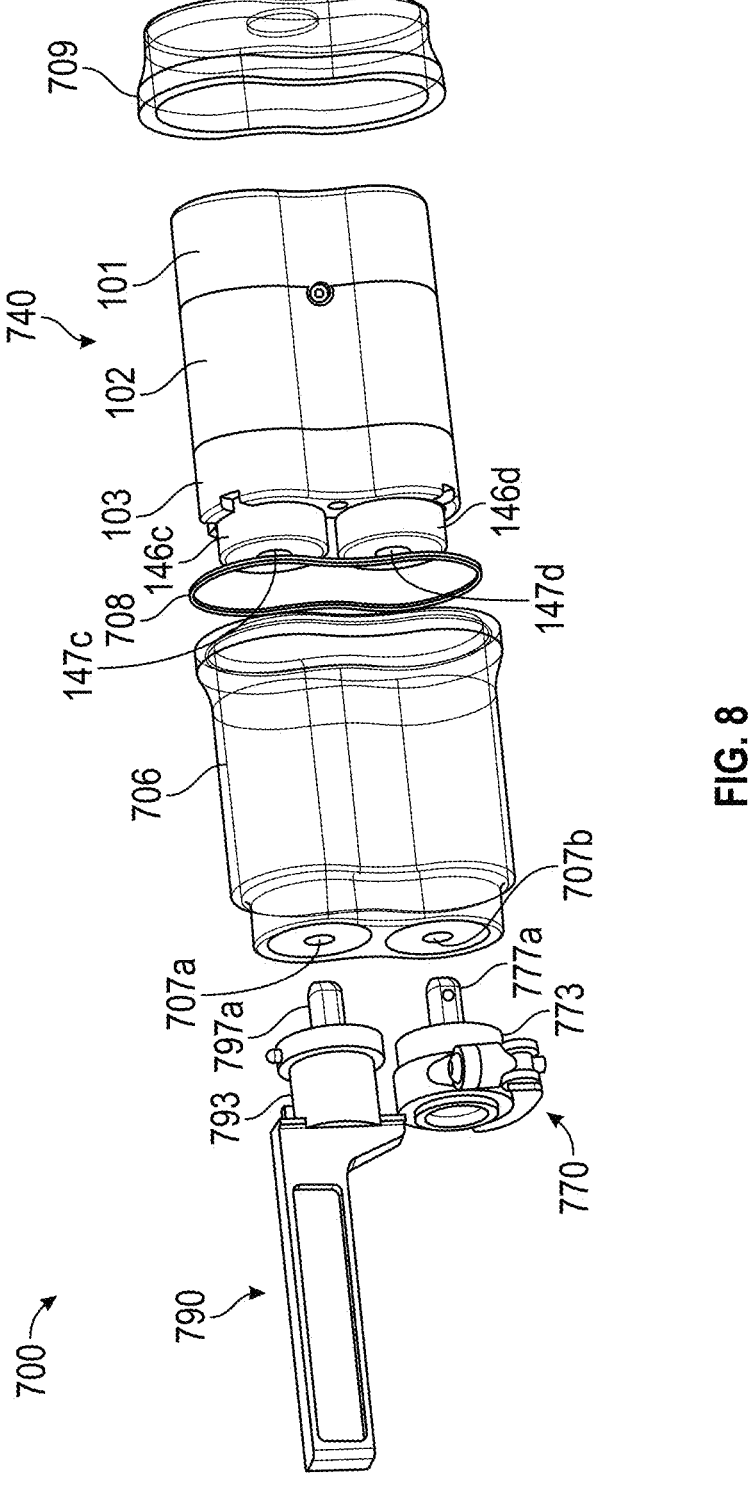
FIG. 8 illustrates an exploded perspective view of the robotic system of FIG. 7, in accordance with some example embodiments.
Figure 9:
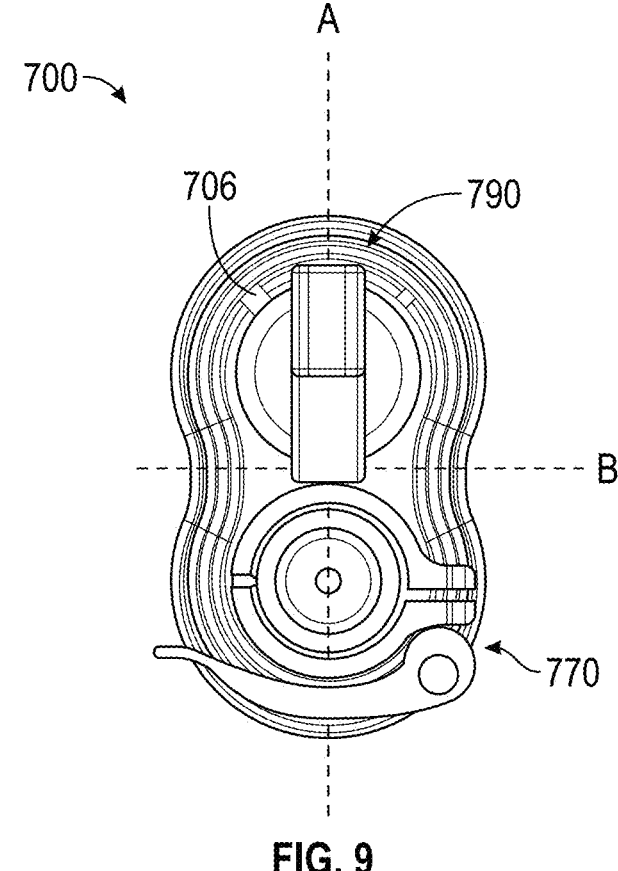
FIG. 9 illustrates a front view of the robotic system of FIG. 7, in accordance with some example embodiments.

FIG. 7 illustrates a perspective view of a robotic system 700 for orthopedic surgery, in accordance with some example embodiments. FIG. 8 illustrates an exploded perspective view of this robotic system. System 700 may be substantially identical to system 100 previously described in connection with any of FIGS. 1-6, except as disclosed below.

Motor pack 740 may be substantially identical to motor pack 140 except that first and second output drive shafts 146a, 146b are replaced with respective first and second output drive shafts 146c, 146d, which comprise respective apertures 147c, 147d rather than posts 147a, 147b.

In the embodiment of FIGS. 7-10, system 700 comprises a housing or case with a sterile outer surface comprising a first portion 706 coupled and/or couplable to a second portion 709. A sealing member 708 (e.g., an o-ring) is disposed between mating edges of first and second portions 706, 709 of the sterile enclosure. The sterile enclosure is configured to house motor pack 740 therein, while allowing coupling and decoupling of one or more tools to motor pack 740. Accordingly, a distal end of first portion 706 comprises a first aperture 707a and a second aperture 707b, each configured to receive at least a portion of those one or more tools. Accordingly, first and second apertures 707a, 707b may be considered entry ports in the sterile casing, configured for coupling sterile tools (e.g., 170, 770, 190, 990) to motor unit 140, 740 (which in some embodiments may not be entirely sterile) disposed inside the sterile casing. Accordingly, when motor unit 140, 740 is disposed within the sterile casing, output shaft couplers 146a, 146b or 146c, 146d are positioned in line with, and adjacent to, first and second apertures 707a, 707b.

A surgical cut guide assembly 790 is substantially identical to surgical cut guide assembly 190 except, instead of a proximal end of cutting guide body 793 being configured to receive distal ends of lugs 105 (and in some embodiments also post 147a) of first output shaft coupler 146a, a proximal end of a similar cutting guide body 793 comprises a post 797a configured to be secured into aperture 147c of first output shaft coupler 146c, through first aperture 707a of first portion 706 of the sterile enclosure. Additionally, the cut guide portion is slidably positionable along a dovetail in 793 and secured via a locking wedge initiated by a locking screw.

A ball joint adjustment and locking mechanism 770 is substantially identical to ball joint adjustment and locking mechanism 170 except, instead of a proximal end of first locking portion 173 being configured to receive distal ends of lugs 105 (and in some embodiments also post 147b) of second output shaft coupler 146b, a proximal end of a similar first locking portion 773 comprises a post 777a configured to be secured into aperture 147d of second output shaft coupler 146d, through second aperture 707b of first portion 706 of the sterile enclosure.

Figure 10:
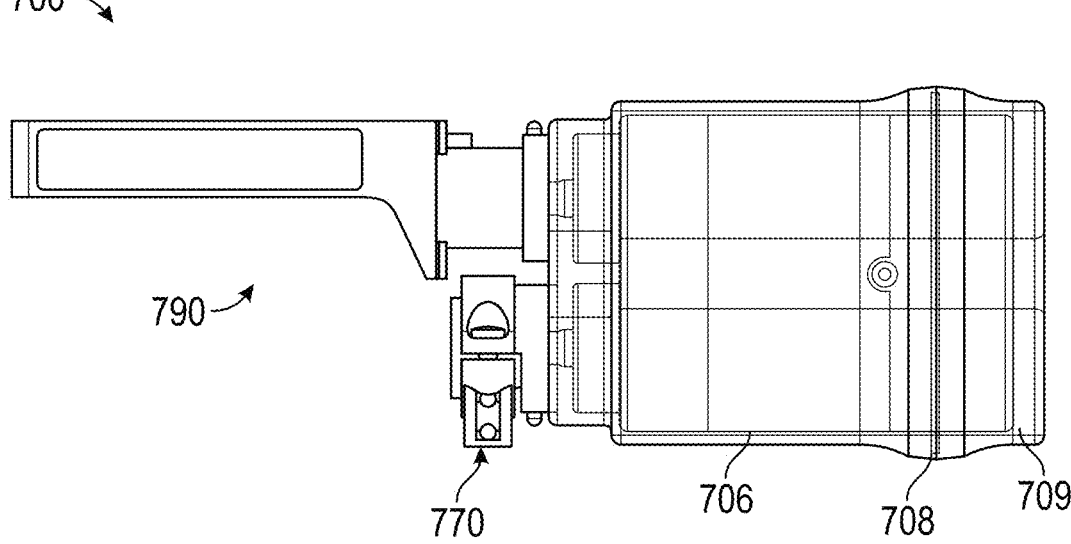
FIG. 10 illustrates a side view of the robotic system of FIG. 7, in accordance with some example embodiments.

FIG. 10 illustrates a side view of robotic system 700 of FIG. 7 with surgical cut guide assembly 790 and ball joint adjustment and locking mechanism 770 coupled as described above. As illustrated in the front view of FIG. 9, robotic system 700 may have a substantially symmetrical shape about a vertical axis "A". In some embodiments, robotic system 700 may have a substantially symmetrical shape about a horizontal axis "B". For example, a cross-section of system 700 when viewed from the front may be substantially similar to that of an "8" or of to that of two circles only partially overlapping. While not explicitly shown in the figures, motor pack 140, 740 may also have similar symmetries about a respective vertical and/or horizontal axis.

Figure 11A:
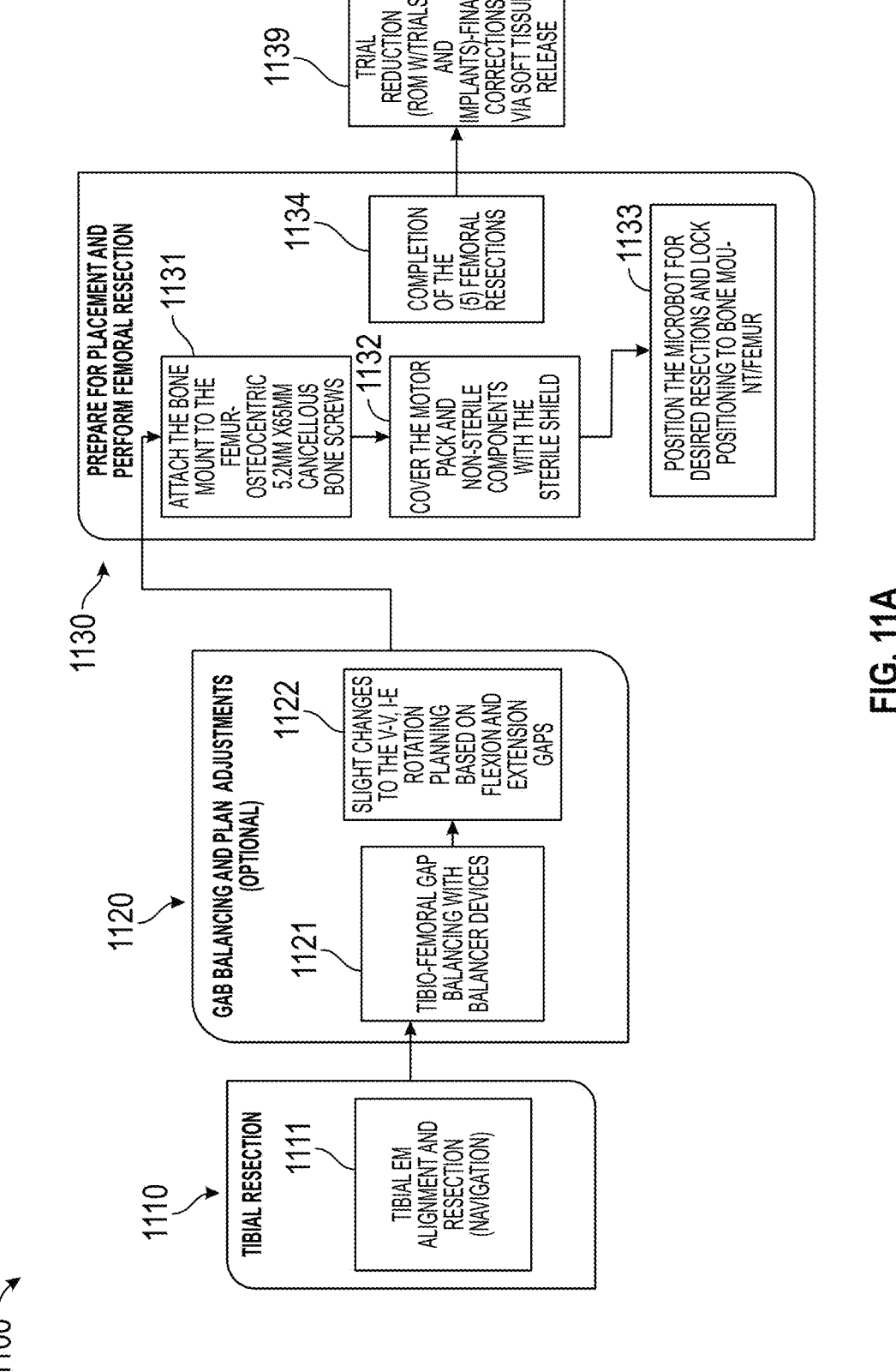
FIG. 11A illustrates a flow diagram of a process for utilizing a robotic system for orthopedic surgery, in accordance with some example embodiments.
Figure 11B:
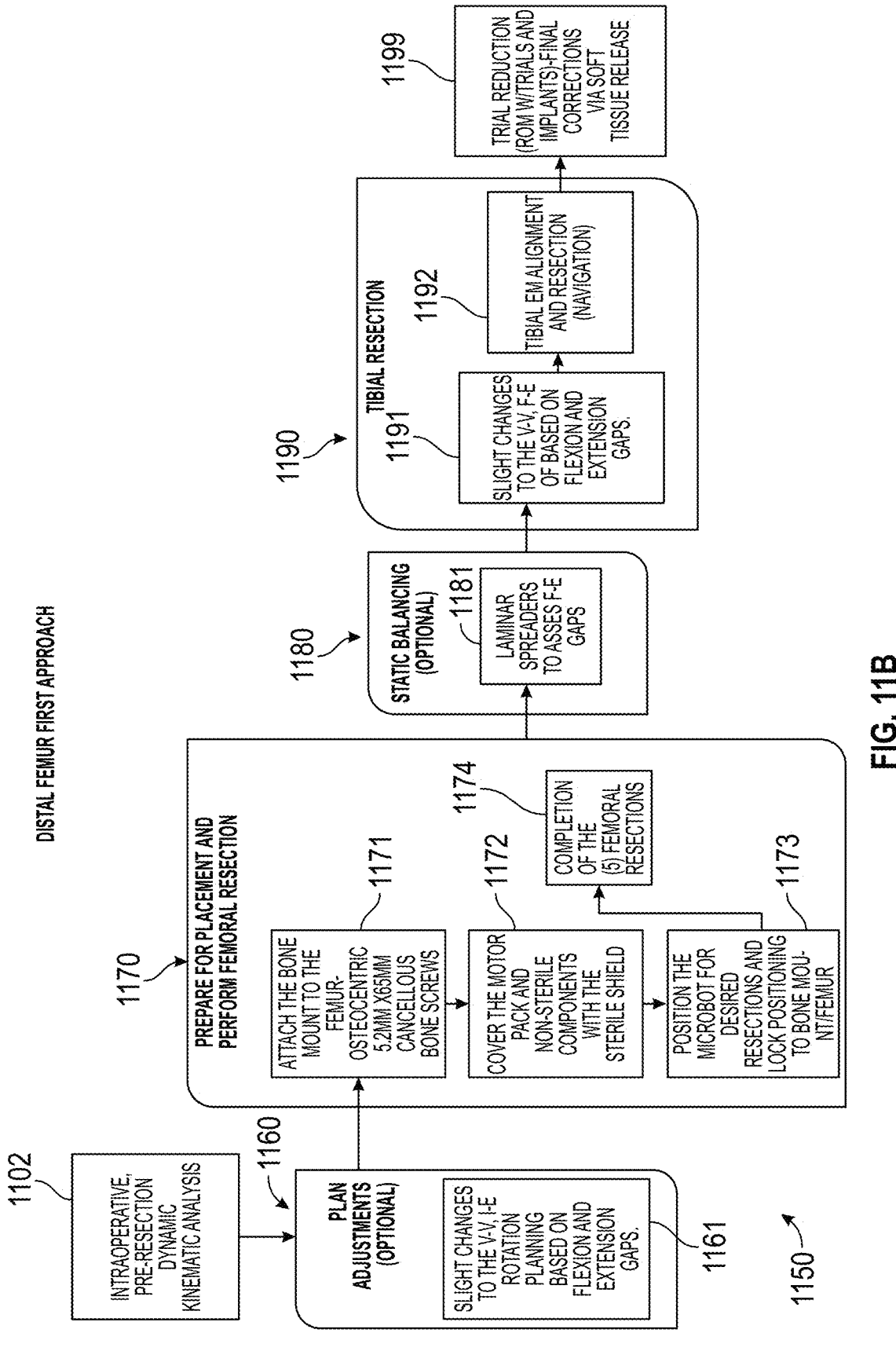
FIG. 11B illustrates a flow diagram of another process for utilizing a robotic system for orthopedic surgery, in accordance with some example embodiments.

FIGS. 11A and 11B illustrate flow diagrams of processes for utilizing a robotic system for orthopedic surgery, in accordance with some example embodiments. Any robotic system 100, 700 described herein may be utilized in such a process or method, or any related process or method.

At 1102, an intraoperative, pre-resection dynamic kinematic analysis is performed on the patient. Then, either a proximal tibia first approach 1100 or a distal femur first approach 1150 may be taken.

In the proximal tibia first approach 1100 of FIG. 11A, at 1110, tibial resection occurs, during which, at 1111, EM alignment and resection is carried out (e.g., navigation). At 1120, gap balancing and plan adjustments are then optionally performed. For example, at 1121, tibio-femoral gap balancing is carried out with bellows balancer devices. Then, at 1122, slight changes to the V-V, I-E rotation planning may be carried out based on flexion and extension gaps. Then, at 1130, preparation for placement and performance of femoral resection is carried out. For example, at 1131, bone mount 180 is attached to the femur utilizing, e.g., osteocentric 5.2 mm×65 mm cancellous bone screws. Then, at 1132, motor pack 140, 740 and non-sterile components are covered with sterile barrier 130 (and/or the sterile enclosure comprising first portion 706, second portion 709 and o-ring 708). Then, at 1133, system 100, 700 is positioned for desired resection and ball joint adjustment and locking mechanism 170, 770 is locked. Then, at 1134, completion of the (5) femoral resections is carried out. At 1139, trial reduction (ROM with trials and implants are carried out and any final corrections are made via soft tissue release.

In the distal femur first approach 1150 of FIG. 11B, at 1160, optional plan adjustments may be carried out. For example, at 1161, slight changes to the V-V, I-E rotation planning may be made based on flexion and extension gaps. Then, at 1170, preparation for placement and performance of femoral resection is carried out. For example, at 1171, bone mount 180 is attached to the femur utilizing, e.g., osteocentric 5.2 mm×65 mm cancellous bone screws. Then, at 1172, motor pack 140, 740 and non-sterile components are covered with sterile barrier 130 (and/or the sterile enclosure comprising first portion 706, second portion 709 and o-ring 708). Then, at 1173, system 100, 700 is positioned for desired resection and ball joint adjustment and locking mechanism 170, 770 is locked. Then, at 1174, completion of the (5) femoral resections 1134 is carried out. Then, at 1180, optional static balancing is carried out. For example, at 1181, laminar spreaders may be utilized to assess F-E gaps. Then, at 1190, tibial resection is carried out. For example, at 1191, slight changes to the V-V, F-E of the cut may be made based on flexion and extension gaps. At 1192, tibial EM alignment and resection is carried out (navigation). At 1199, trial reduction (ROM with trials and implants are carried out and any final corrections are made via soft tissue release.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A robotic system for orthopedic surgery comprising:
a first motor comprising a first motor shaft defining a first rotation axis;
a first output drive shaft coupled to the first motor shaft;
a second motor coupled to the first motor and comprising a second motor shaft defining a second rotation axis parallel to the first rotation axis;
a second output drive shaft coupled to the second motor shaft;
a surgical tool or surgical tool guide integral with, coupled to, and/or configured to be coupled to an end of the first output drive shaft; and a first portion of a ball and socket joint integral with, coupled to, and/or configured to be coupled to an end of the second output drive shaft, and a bone mount, wherein the bone mount comprises a second portion of the ball and socket joint.

2. The system of claim 1, wherein the first portion of the ball and socket joint comprises a socket portion of the ball and socket joint.

3. The system of claim 2, wherein the socket portion of the ball and socket joint comprises:

a first locking portion pivotally coupled to a second locking portion via a hinge pin; and a locking lever configured to clamp the first and second locking portions down on a ball receiving portion.

4. The system of claim 2, wherein the second portion of the ball and socket joint comprises a ball portion of the ball and socket joint.

5. The system of claim 4, wherein the socket portion of the ball and socket joint comprises:

a first locking portion pivotally coupled to a second locking portion via a hinge pin; and a locking lever configured to clamp the first and second locking portions down on a ball receiving portion to fix the ball portion of the bone mount inside the ball receiving portion.

6. The system of claim 5, wherein the ball portion is configured to extend from a surface of the bone mount opposite a bone-facing surface of the bone mount.

7. The system of claim 1, wherein:

rotation of the first output drive shaft causes adjustment of an angular orientation of the surgical tool or surgical tool guide with respect to the first motor; and rotation of the second output drive shaft causes adjustment of an angular orientation of the first motor with respect to the bone mount.

8. The system of claim 1, wherein a ball portion and a socket portion of the ball and socket joint are friction fit stabilized for hand adjustment of the relative orientations of first motor, the second motor, and the bone mount.

9. A robotic system for orthopedic surgery comprising:

a first motor comprising a first motor shaft defining a first rotation axis;

a first output drive shaft coupled to the first motor shaft;

a second motor coupled to the first motor and comprising a second motor shaft defining a second rotation axis parallel to the first rotation axis;

a second output drive shaft coupled to the second motor shaft;

a surgical tool or surgical tool guide integral with, coupled to, and/or configured to be coupled to an end of the first output drive shaft; and a first portion of a ball and socket joint integral with, coupled to, and/or configured to be coupled to an end of the second output drive shaft;

a first position encoder configured to monitor a relative angular orientation of the surgical tool or the surgical tool guide with respect to the first motor; and a second position encoder configured to monitor a relative angular orientation of the first motor with respect to a bone of the patient.

10. A robotic system for orthopedic surgery comprising:

a first motor comprising a first motor shaft defining a first rotation axis;

a first output drive shaft coupled to the first motor shaft;

a second motor coupled to the first motor and comprising a second motor shaft defining a second rotation axis parallel to the first rotation axis;

a second output drive shaft coupled to the second motor shaft;

a surgical tool or surgical tool guide integral with, coupled to, and/or configured to be coupled to an end of the first output drive shaft; and a first portion of a ball and socket joint integral with, coupled to, and/or configured to be coupled to an end of the second output drive shaft; and wherein the surgical tool or surgical tool guide comprises a slot for a saw blade.

11. The system of claim 10, wherein the surgical tool or surgical tool guide further comprises a hole for a drill.

12. A robotic system for orthopedic surgery comprising:

at least one motor;

at least one motor output shaft coupled to the at least one motor, wherein the at least one motor output shaft comprises a non-circular strain wave generator;

a stationary circular ring gear around the at least one motor output shaft;

a deformable gear positioned between the stationary circular ring gear and the non-circular strain wave generator;

an output shaft integral with, coupled to, and/or configured to be coupled to the deformable gear;

a surgical tool integral with, coupled to, and/or configured to be coupled to the deformable gear.

13. The system of claim 12, further comprising at least a first position encoder configured to monitor a relative angular orientation of the at least one motor with respect to a bone of a patient.

14. The system of claim 12, further comprising a surgical tool or surgical tool guide integral with, coupled to, and/or configured to be coupled to the at least one motor.

15. The system of claim 14, wherein the surgical tool or surgical tool guide comprises a slot for a saw blade.

16. The system of claim 15, wherein the surgical tool or surgical tool guide further comprises a hole for a drill.

17. The system of claim 12, wherein the at least one motor comprises: a first motor comprising a first motor shaft defining a first rotation axis; a second motor coupled to the first motor and comprising a second motor shaft defining a second rotation axis parallel to the first rotation axis.

18. The system of claim 17, further comprising:

a first output drive shaft coupled to the first motor shaft;

a second output drive shaft coupled to the second motor shaft;

a surgical tool or surgical tool guide integral with, coupled to, and/or configured to be coupled to an end of the first output drive shaft.

19. The system of claim 18, further comprising a first portion of a ball and socket joint integral with, coupled to, and/or configured to be coupled to an end of the second output drive shaft.

20. A robotic system for orthopedic surgery comprising:

a first motor comprising a first motor shaft defining a first rotation axis;

a first output drive shaft coupled to the first motor shaft;

a second motor coupled to the first motor and comprising a second motor shaft defining a second rotation axis parallel to the first rotation axis;

a second output drive shaft coupled to the second motor shaft;

a surgical tool or surgical tool guide integral with, coupled to, and/or configured to be coupled to an end of the first output drive shaft; and a first portion of a ball and socket joint integral with, coupled to, and/or configured to be coupled to an end of the second output drive shaft, wherein the end of each of the first and second output shafts comprises a post configured to engage with a respective aperture in a proximal end of one of the surgical tool or surgical tool guide and the first portion of the ball and socket joint, or wherein the end of each of the first and second output shafts comprises an aperture configured to receive a respective post extending from a proximal end of one of the surgical tool guide and the first portion of the ball and socket joint.

\* \* \* \* \*